(12) United States Patent
Li

(10) Patent No.: US 12,428,385 B2
(45) Date of Patent: Sep. 30, 2025

(54) COMPOSITION OF A LIPOPHILIC AGENT FOR SOLUTION PHASE SYNTHESIS OF BIOMOLECULES

(71) Applicant: Yongfu Li, Corvallis, OR (US)

(72) Inventor: Yongfu Li, Corvallis, OR (US)

(73) Assignee: Brotide Core, LLC, Corvallis, OR (US)

( * ) Notice: Subject to any disclaimer, the term of this patent is extended or adjusted under 35 U.S.C. 154(b) by 89 days.

(21) Appl. No.: 17/748,292

(22) Filed: May 19, 2022

(65) Prior Publication Data
US 2023/0373936 A1      Nov. 23, 2023

(51) Int. Cl.
| | | |
|---|---|---|
| *C07D 471/04* | (2006.01) | |
| *C07D 251/54* | (2006.01) | |
| *C07K 1/04* | (2006.01) | |

(52) U.S. Cl.
CPC ......... *C07D 251/54* (2013.01); *C07D 471/04* (2013.01); *C07K 1/042* (2013.01)

(58) Field of Classification Search
None
See application file for complete search history.

(56) References Cited

PUBLICATIONS

Lai et al., Nanomaterials of Triazine-Based Dendrons: Convergent Synthesis and Their Physical Studies. Organic Letters, 2006, 8, 1541-1544.*
Grant & Hackh's Chemical Dictionary (5th Ed. 1987) at p. 148.*
Chemical Abstract Registry No. 715644-67-0, indexed in the Registry File on STN CAS Online Jul. 23, 2004.*
Apartsin et al., pH-Sensitive Dendrimersomes of Hybrid Triazine-Carbosilane Dendritic Amphiphiles-Smart Vehicles for Drug Delivery. Nanomaterials, 2020, 10, p. 1-15.*

* cited by examiner

*Primary Examiner* — Po-Chih Chen

(57) ABSTRACT

Disclosed is a lipophilic agent comprising a triazine core having lipophilic groups for organic synthesis. The lipophilic agent soluble in one system of solvent(s) wherein the lipophilic agent is participated in a chemical reaction but insoluble by adding a miscible poor solvent to change solution composition after the reaction completes. The lipophilic agent facilitates process improvement wherein practical operation only involves mixing with reactants in solution followed by precipitating with change of solution composition followed by filtering to obtain the precipitated solid, simplifying the purification by isolating the desired solid. The operation is reproducible along the progress in a multi-step synthesis, allowing pure intermediates and pure product as a solid to be rapidly obtained with ease and certainty. This invention can thus accelerate research and development of pharmaceutical biomolecules, representing a tremendous step forward for boosting productivity and greening chemical industry.

3 Claims, No Drawings

COMPOSITION OF A LIPOPHILIC AGENT FOR SOLUTION PHASE SYNTHESIS OF BIOMOLECULES

FIELD OF THE INVENTION

The present invention relates to a lipophilic agent for organic synthesis and a method of organic synthesis reaction using the lipophilic agent, and in more detail, it relates to a lipophilic agent comprising a triazine core having lipophilic groups for organic synthesis which is a compound which rapidly and reproducibly changes from a soluble state to a solid state due to a change in solution composition, which is provided as a compound acting as a reaction substance in an organic synthesis reaction, or which is provided as a compound which bonds to unreacted compounds or byproducts in an organic synthesis reaction, which can be easily separated from the reaction system after the reaction.

BACKGROUND OF THE INVENTION

In traditional organic chemical reaction processes, fundamental techniques, after a reaction completes, are either to isolate a desired product or to remove unwanted excess reagents, byproducts, catalysts and the like from a mixture of reaction solution. Fortunate cases are rare wherein the desired product solidifies (or crystallizes) from the reaction mixture to give the desired product in pure form. A majority of organic synthesis belongs to reactions wherein a desired product may be a liquid, or an oily material by its nature, or a solid after it is purified. A liquid product can probably be obtained by distillation or high vacuum distillation, the process requiring the liquid product being thermally stable. For those compounds as oily material or practically impossible to solidify, column chromatography commonly using silica gel would be the method of choice for purification. However, depending on the mobility of the desired product on the silica gel and the complexity in the presence of other unwanted components in the mixture, a substantial amount of silica gel and a large volume of solvent(s) have to be consumed which result in rising cost for the production of the compound and for subsequent treatment of the waste solvent(s). For a compound which is a solid after being purified, it may take great effort to solidify from a mixture of reaction in presence of a variety of reactants and byproducts. Conditions for solidification (or crystallization) vary for different compounds. In many cases, conditions for solidification (or crystallization) are found by experience based on trial and error. Especially, in successive multi-step synthesis, because it is necessary to consider the solidification (or crystallization) conditions based on the characteristic properties of the compounds synthesized in each of the steps, process development becomes very expensive and time consuming.

In order to solve such problems including making successive compounds each as a solid in a multi-step synthesis, in the prior art, there was known a means of using a chemically functionalized reagent on solid support such as polystyrene resin, polyethylene glycol resin and the like. This method of synthesis on a solid phase support allows the reaction to proceed each step attached to the solid support, providing the convenience of removing the unwanted excess reagents, byproducts, catalysts and the like by simply washing the solid phase with certain solvent(s). While benefits of solid phase synthesis includes high efficiency and increased speed, the drawback of solid phase synthesis has multiple folds: (a) use of excess amount of reaction reagents is necessary for complete conversion of the reaction owing to low reactivity due to the heterogeneous nature of the solid phase, and (b) significant volumes of solvents are needed for each reaction and washing. These are especially problematic for a large-scale synthesis owing to the limited capacity of loading of the functionalized reagent on solid support and the significant overall cost.

Altogether, for a synthesis reaction in a traditional solution phase, isolation of the desired compound requires skill and experience and can be laborious, whereas for a synthesis reaction on solid phase support, a large-scale synthesis is limited due to the limited loading capacity of the functionalized reagent and the heterogeneous nature of the solid phase which requires large excess of reagents for the reaction and large volume of solvent(s) for each reaction and washing.

The key to overcome the corresponding disadvantages of each of the methods described above, namely, the difficulty in isolating a desired compound in the traditional solution phase synthesis and the cost of using excess reagents and solvents in the solid phase synthesis is to invent a new composition which can combine the advantages of each of the above two methods, namely, a high reactivity from the traditional solution phase synthesis and an effective separation technique from the solid phase synthesis. In other words, if a reaction can be conducted in a homogeneous solution and after completion of the reaction, a desired product or unnecessary byproduct(s) and compounds can be isolated as a solid, the above-mentioned limitations can be avoided. Early work in this area employed polystyrenes (PS) or polyethylene glycols (PEG) as soluble tags instead of insoluble resins for peptide synthesis where the soluble tag provided carboxyl-terminal protective groups for the growing peptides. Both couplings and deprotections were carried out on soluble tags in homogeneous solutions and non-tethered entities were rinsed away by precipitation of the tagged growing peptides. However, owing to the polymeric nature of PS or PEG which is a complex mixture with different lengths of chained units, structural characterization and quality assurance became practically impossible. Tag-assisted solution phase synthesis was further improved by employing tris(alkoxy)benzyl alcohols as a soluble tag. The tris(alkoxy)benzyl tags are relatively small molecules with defined structure and therefore, each step of reaction could be monitored by thin layer chromatography (TLC) or other analytical methods and the characterization of the tagged growing compounds was possible by nuclear magnetic resonance (NMR), mass spectroscopy (MS) and/or other analytical methods. For example, such hydrophobic benzyl alcohols as soluble tags were used for peptide synthesis. Both couplings and deprotections are carried out on the tags in a homogeneous solution using a solvent such as tetrahydrofuran (THF) and after the reaction completes, non-tethered entities are rinsed away by precipitating the tagged growing peptides with a different solvent such as acetonitrile. However, owing to the structural characteristics of phenolic ethers in the alkoxybenzyl tags, the phenolic moiety tends to undergo electrophilic aromatic substitution, resulting in undesired change of the phenolic core structure. Also, owing to the electronic donating property of multiple alkoxy groups to the phenolic core structure, alkoxybenzyl tags are inherently sensitive to various conditions. For example, 2,4,5-tris(alkoxy) benzyl, 3,4,5-tris(alkoxy) benzyl, and 2,4-di(alkoxy) benzyl compounds cannot resist acidic treatment or oxidant treatment, and 3,5-di(alkoxy) benzyl, 2,5-di(alkoxy) benzyl compounds are sensitive to light exposure, leading to degradation of the tag or premature cleavage in a multi-step synthesis. Sensitivity of the tag to acid, oxidant or light is detrimental and limits the applicability of the tag wherein acid, oxidizing reagent, or light exposure is involved in making intermediates in multi-step synthesis.

Therefore, a broadly and generally stable agent is in need which can not only reproducibly change from a soluble state to a solid state with changes in solution composition, but also flexibly install a variety of linkers for specific synthesis purposes. Such an agent is soluble in one system of solvent(s) so that the agent can tether any suitable compound for successive synthetic reactions and is insoluble in other system of solvent(s) so that the product can be obtained "easily" as a pure solid. The agent can thus be used in a multi-step synthesis process so that pure intermediates and pure product as a solid can be routinely and rapidly obtained with ease and certainty.

DISCLOSURE OF THE INVENTION

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the present specification are hereby cited by reference so as to describe and disclose constructed products and methodology described in, for example, publications usable in relation to the described invention.

I. ABBREVIATION AND DEFINITIONS

Before describing detailed embodiment of the invention, it will be useful to set forth abbreviations and definitions that are used in describing the invention. The definitions set forth apply only to the terms as they are used in this patent. The following description of the preferred embodiment and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature.

In describing and claiming the present invention, the following terminology will be used in accordance with the definitions set out below.

"Organic synthesis" is a special branch of chemical synthesis and is concerned with the intentional construction of organic compounds. Organic molecules are often complex and their synthesis involves a successive synthetic steps from simple, commercially available starting materials such as petrochemicals or natural precursors. Organic synthesis is performed one step after another until the molecule is complete; the chemical compounds made in each step before the final step are called synthetic intermediates and the chemical compound made in the final step is called a product. Each step of a synthesis involves a chemical reaction and reagents and conditions for each of these reactions must afford an adequate yield of a pure product.

"Column chromatography" in chemistry is a chromatography method used to isolate a single chemical compound from a mixture. Chromatography can separate substances based on differential adsorption of compounds to the adsorbent; compounds move through the column at different rates, allowing them to be separated into fractions. The technique is widely applicable, as many different adsorbents (normal phase, reversed phase, or others) can be used with a wide range of solvents. The most common adsorbent for column chromatography is silica gel. Silica gel is an amorphous and porous form of silicon dioxide (silica), consisting of an irregular tri-dimensional framework of alternating silicon and oxygen atoms with nanometer-scale voids and pores. There is an important ratio between the adsorbent weight and the dry weight of the mixture containing the to-be-purified desired compound that can be applied onto the column. For silica gel column chromatography, this ratio lies within 20:1 to 100:1, depending on how close to each other the desired compound is being eluted. A solvent or a mixture of solvents is used as eluent to move the compounds through the column. Column chromatography is an extremely time-consuming stage in any laboratory and can quickly become the bottleneck for any process development due to the solvent(s) to be consumed and labor to be engaged.

"Solid phase synthesis" is a method in which molecules are covalently bound to a functionalized linker on a solid support material and synthesized step-by-step in a single reaction vessel utilizing selective protecting group chemistry. Benefits compared with normal synthesis in a solution state include high efficiency, high throughput, increased simplicity and speed. The reaction can be driven to completion and high yields through the use of excess reagent. This method is commonly used for the synthesis of biomolecules such as peptides, deoxyribonucleic acid (DNA), ribonucleic acid (RNA), and other molecules that need to be synthesized in a certain alignment. The biomolecules can be obtained by properly cleaving from the solid support.

"Traceless synthesis" represents an intelligent synthetic strategy on soluble or insoluble supports containing a functionalized linker. Compounds synthesized on the support can be released without a trace of the linker that was used to tether the intermediates during the synthesis. Thus, the target products are composed only of the components (atoms, functional groups) inherent to the target structure.

"Biomolecules" refers to bioactive substances including therapeutic compounds or diagnostic agents, as well as lead compounds in a research and development setting. Still further the term is meant to include various probes (e.g., oligonucleotides alone or those having attached imaging agents) and substances effective to alter biological processes within cells. Biomolecules include small organic molecules which refer to a carbon-containing agent having a molecular weight of less than or equal to 1000 Daltons. Biomolecules also include macromolecules which refer to large molecules (molecular weight greater than 1000 Daltons) of biological or synthetic origin, exemplified by, but not limited to, peptides, proteins, oligonucleotides, polynucleotides and analogs thereof such as peptide nucleic acid (PNA).

"Therapeutic compound" refers, without limitation, to any composition that can be used to the benefit of a mammalian species. A number of such agents cause an observable change in the structure, function or composition of a cell upon uptake by the cell. Observable changes include increased or decreased expression of one or more proteins, phosphorylation of a protein or other cell component, inhibition or activation of an enzyme, inhibition or activation of binding between members of a binding pair, an increased rate of synthesis of a metabolite, increased or decreased cell proliferation and the like. Other agents exert therapeutic effects when present in a tissue, even in the absence of cellular entry.

"Diagnostic agent" refers to both diagnostic imaging agents and contrast agents. The following are non-limiting examples of diagnostic agents: radio-labeled substances, substances used in magnetic resonance imaging and molecular sensors.

"Triazine" refers to 1,3,5-triazine as s-triazine which is a class of nitrogen-containing heterocycles. Most triazine derivatives were prepared by using cyanuric chloride as a starting material, taking advantage of its easy manipulation of three independent, readily tunable ring positions, which facilitates sequential nucleophilic substitution reactions with a variety of nucleophiles containing sulfur, oxygen and nitrogen. After nucleophilic substitution replacing all three chlorides with nucleophiles containing sulfur, oxygen, and nitrogen, the triazine heterocycle stays intact as a robust core under a broad range of reaction conditions. The triazine core is thus used as a privileged structure for assembly of Lipophilic anchor (vide infra) of this invention.

"Lipophilic anchor" refers to a lipophilic agent of this invention containing a triazine core having specified "Lipophilic group" (vide infra). The lipophilic agent containing the Lipophilic anchor of this invention has a property of reproducibly changing from a soluble state to a solid state according to changes in the solution composition. In a multi-step synthesis of a biomolecule, each cycle of a reaction step involves simply mixing with reactants in solution followed by precipitating with change of solution composition followed by filtering to obtain the precipitated solid. The cycle can be practically performed over and over again along the progress of a mission of synthesis. Further, the lipophilic agent, after the mission for a multi-step synthesis of a target molecule is accomplished, and proper recovery is achieved to regenerate its original form, can be re-used for a subsequent mission to synthesize the same target molecule or a different target molecule. Thus, the cycles can be technically performed over and over again for virtually unlimited rounds of mission, implicating the significance of its green utility (saving the resources and protecting the environment) for a multi-step synthesis within a mission and for further missions. The lipophilic anchor tethering a suitable linker for synthesis of biomolecules is called "Lipophilic linker", and the lipophilic anchor tethering a reactive site to be used as a part of a target compound is called "Lipophilic reagent". Lipophilic agent includes Lipophilic linker and Lipophilic reagent. Lipophilic agent after reaction with a target compound is called "Lipophilic derivative". The lipophilic agent, and Lipophilic derivative containing Lipophilic anchor are all soluble in one system of solvent(s) and become insoluble after changes of solvent system.

"Lipophilic group" refers to lipophilic groups with a carbon number of 12 to 48 which may have substituent group attaching to a triazine core to form the lipophilic agent of this invention.

II. PROBLEMS TO BE SOLVED BY THE INVENTION

In the process research and development of chemical compounds, especially biomolecules as pharmaceuticals, main efforts are focused on the reaction workup for purification of each intermediate and ultimately final product in a multi-step organic synthesis. Methods of separating as a solid a specified compound mixed in a solution are preferably used. This is because, by solidifying (or crystallizing) only the specified component, separation and/or purification after the reaction are simplified. The solidification (or crystallization) of specified component mixed in a solution in this way is implemented by satisfying defined conditions in the relationship with chemical properties and physical properties of the component, and with the solvent. In many cases, conditions for solidification (or crystallization) are found by experience based on trial and error. In particular, recently, in successive multistage synthesis such as compound library synthesis and the like used in the research and development of pharmaceuticals, after the completion of each reaction, by solidifying (or crystallizing) the desired compounds, the isolation of the solidified (or crystallized) substances becomes easy, and it adds the efficiency to fulfill the process development. Conversely, by solidifying (or crystallizing) the unnecessary compounds, the removal of the solidified (or crystallized) substances becomes easy, and it helps to prevent the processes from becoming complicated. Search for the conditions for solidification (or crystallization) results in very expensive and time-consuming process development. When all the efforts fail to find a process for isolation of the desired compound as a solid, column chromatography becomes the last resort for purification. However, column chromatography is extremely time-consuming and costly due to lot of labor to be engaged and large volume of solvent(s) to be consumed.

In the case of utilizing a reaction using a chemically functionalized reagent on solid support such as polystyrene resin, the reaction point is only at the solid liquid surface, thus the reactivity is often low. This method of synthesis on a solid phase support allows the reaction to proceed each step attached to the solid support, providing the convenience of removing the unwanted excess reagents, byproducts, catalysts and the like by simply washing the solid phase with certain solvent(s). While benefits of solid phase synthesis includes high efficiency and increased speed, the drawback of solid phase synthesis includes: (a) use of excess amount of reaction reagents which is necessary for complete conversion of the reaction, and (b) significant volumes of solvents that are needed for each reaction and washing. These are especially problematic for a large-scale synthesis owing to the limitation of the scale and the significant overall cost.

The present invention was made in view of the above problems and has the objective of providing a lipophilic agent for organic synthesis and a method of organic synthesis reaction using the lipophilic agent. Such a lipophilic agent is soluble in one system of solvent(s) so that the lipophilic agent can tether any suitable compound for synthetic reactions in homogeneous solution and is insoluble in other system of solvent(s) so that the desired compounds can be isolated as a solid. Alternatively, unnecessary compounds can thus be removed by forming a solid from the solution phase after the completion of the reaction, preventing the purification process from becoming complicated.

III. LIPOPHILIC AGENT

Embodiment of the invention are described in detail below. These embodiments do not in any way limit the lipophilic agent for the method of organic synthesis reaction using the lipophilic agent of the present invention, and appropriate modifications can be made within the scope of the objectives of the present invention.

Lipophilic Anchor

"Lipophilic anchor" refers to a lipophilic agent of this invention including a triazine core having specified Lipophilic groups. Lipophilic anchor according to the present embodiment is shown by Chemical Formula (1)

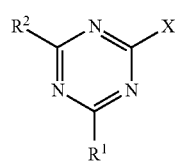

(1)

where Lipophilic groups $R^1$ and $R^2$ may be same or different, and are independently selected from the group comprising alkyl group with a carbon number of 12 to 48 which may have a substituent group, alkoxyl group with a carbon number of 12 to 48 which may have a substituent group, aryl group with a carbon number of 12 to 48 which may have a substituent group, thioalkyl group with a carbon number of 12 to 48 which may have a substituent group, alkylamino group with a carbon number of 12 to 48 which may have a substituent group, and dialkylamino group with a carbon number of 12 to 48 which may have a substituent group, and $R^1$ and $R^2$ contain at least two Lipophilic groups including alkyl group, alkoxyl group, thioalkyl group, and alkylamino group or dialkylamino group with a carbon number of 12 to 48 which may have a substituent group. In the formula, X represents an active site of the lipophilic agent having one or more atoms selected from the group comprising carbon atom, halogen atom, nitrogen atom, oxygen atom, silicon atom or sulfur atom. Thus, Lipophilic anchor links with an active site X to form a lipophilic agent. The lipophilic agent comprising a suitable linker for synthesis of biomolecules is called "Lipophilic linker", and the lipophilic agent comprising a reactive site to be used as a part of a target compound is called "Lipophilic reagent", and Lipophilic agent after reaction with a target compound is called "Lipophilic derivative".

Because the above compounds have at least two Lipophilic groups selected from the group comprising alkyl group, alkoxyl group, thioalkyl group, alkylamino group or dialkylamino group with a carbon number of 12 to 48 which may have a substituent group, they can have sufficient lipophilicity, and can be dissolved in a wide range of organic solvents. Thus, the lipophilic agent and resultant Lipophilic derivative from reaction of the lipophilic agent with a target compound have a property of reproducibly changing from a soluble state to a solid state according to changes in the solution composition. Further, structure of Lipophilic anchor of the lipophilic agent is stable with respect to acid treatment, basic treatment, oxidative treatment, or light exposure, and is especially suitable for broad range of organic synthesis.

Active Site

In the above Chemical Formula (1), X indicates an active site having at least one atom selected from the group comprising halogen including fluorine, chlorine, bromine and iodine, carbon, oxygen, sulfur, and nitrogen atom. Here, X may also have a structure indicated by the following Chemical Formulas (1P, P indicating a secondary amine derived from piperazine), (1C, C indicating a carboxyl group derived from isonipecotic acid), or (1H, H indicating a hydroxyl group derived from 4-piperidinemethanol).

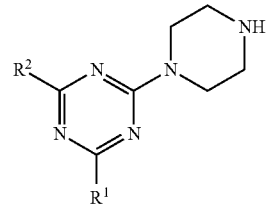

(1P)

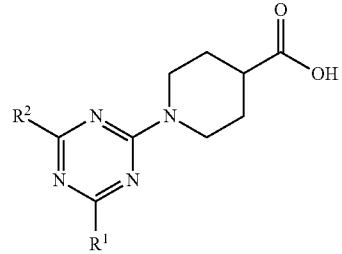

(1C)

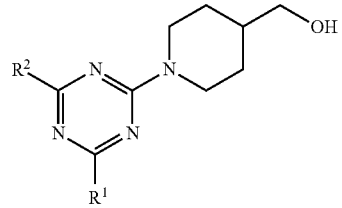

(1H)

Further, the lipophilic agent (1P) can be derivatized to form the corresponding amide bond with suitable reagent to install functional Lipophilic linkers. Common linkers include, but are not limited to, the following. The functionalized linker may have a structure indicated by the following Chemical Formulas (1A), (1B), (1W), (1T), (1R). A is to indicate a carboxylic acid functional group derivatized from succinic acid, B is to indicate a benzyl alcohol functional group derivatized from 4-hydroxymethylbenzoic acid, and W is to indicate hydroxyl functional group containing p-oxybenzyl alcohol, T is to indicate a trityl alcohol moiety which needs to be converted into chloro derivative before use, R is to indicate Rink Amide moiety containing an amino functional group. The nature of the linker determines the chemistry to be used in organic synthesis, and especially the conditions under which the products can be cleaved from Lipophilic linker.

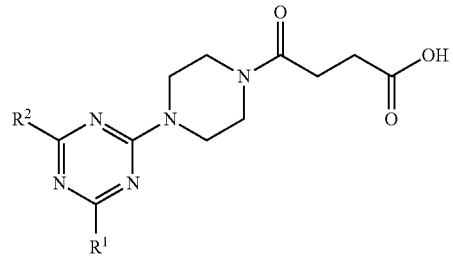

(1A)

(1B)

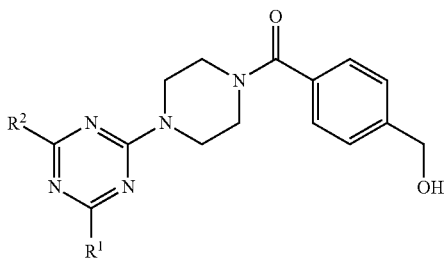

(1W)

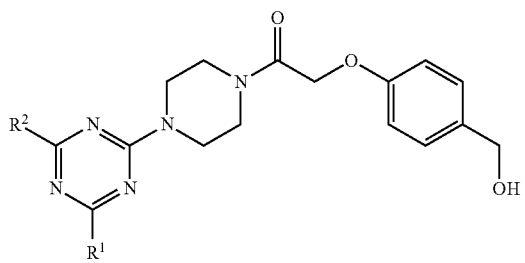

(1T)

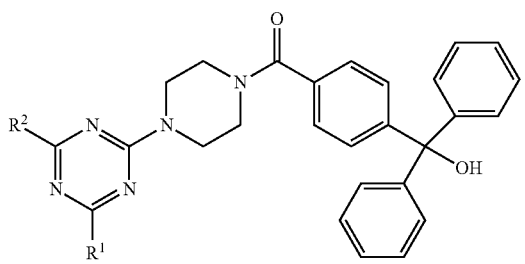

(1R)

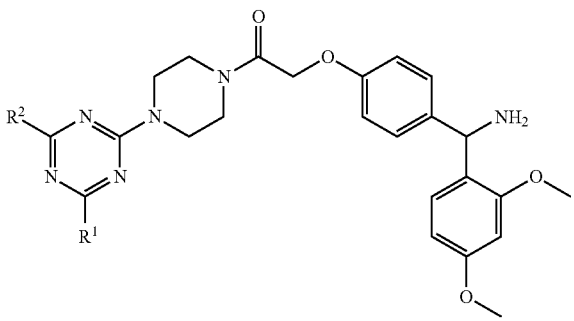

IV. MEANS FOR SOLVING THE PROBLEMS

The present invention relates to the finding that for organic synthesis by using a lipophilic agent including a triazine core having specified lipophilic groups, and having a property of reproducibly changing from a soluble state to a solid state according to changes in the solution composition, it is possible to carry out the purification of desired intermediates and final product as a solid, or alternatively, it is possible to carry out the separation of unnecessary compounds from the solution phase after the completion of the reaction. The process is easy and cost-effective.

The composition of the lipophilic agent includes a triazine core having specified lipophilic groups each with a carbon number of 12 to 48 which may have a substituent group and an active site. The triazine core having lipophilic groups which functions as a lipophilic anchor is called "Lipophilic anchor", and the lipophilic group with a carbon number of 12 to 48 which may have a substituent group is called "Lipophilic group".

Specifically, the present invention provides the following.

The first aspect of the invention provides a lipophilic agent including a triazine core which can be used for organic synthesis reactions, shown in the below Chemical Formula (1), having a property of reproducibly changing from a soluble state to a solid state according to changes in solution composition.

(1)

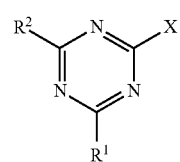

In the formula, Lipophilic group $R^1$ and $R^2$ may be same or different, and are independently selected from the group comprising alkyl group with a carbon number of 12 to 48 which may have a substituent group, alkoxyl group with a carbon number of 12 to 48 which may have a substituent group, aryl group with a carbon number of 12 to 48 which may have a substituent group, thioalkyl group with a carbon number of 12 to 48 which may have a substituent group, alkylamino group with a carbon number of 12 to 48 which may have a substituent group, and dialkylamino group with a carbon number of 12 to 48 which may have a substituent group. Further, in the formula, X represents an active site of the lipophilic agent having one or more atoms selected from the group comprising carbon atom, halogen atom, nitrogen atom, oxygen atom, silicon atom or sulfur atom. Lipophilic anchor linked to an active site is called "lipophilic agent". The lipophilic agent comprising a suitable linker for synthesis of biomolecules is called "Lipophilic linker", and the lipophilic agent comprising a reactive site to be used as a part of a target compound is called "Lipophilic reagent", and Lipophilic agent after reaction with a target compound is called "Lipophilic derivative".

According to the lipophilic agent according to the first aspect, in addition to having an active site having one or more atoms selected from the group comprising halogen, carbon, oxygen, sulfur, or nitrogen atom, it also has, as substituent groups on the triazine ring, at least two of the one of the following: alkyl group with a carbon number of 12 to 48 which may have a substituent group, alkoxyl group with a carbon number of 12 to 48 which may have a substituent group, thioalkyl group with a carbon number of 12 to 48 which may have a substituent group, alkylamino group with a carbon number of 12 to 48 which may have a substituent group, or dialkylamino group with a carbon number of 12 to 48 which may have a substituent group. Because of this, the lipophilic agent can be dissolved uniformly with high concentration in many organic solvents, and it can react with a high degree of reactivity with a target compound in many organic solvents.

Further, the lipophilic agent according to the first aspect can also be used mainly as a nucleophilic scavenger, electrophilic scavenger, synthesis building block, condensation agent, or traceless synthesis. Namely, it can be used in a wide range of applications, as a reaction substance for unnecessary substances such as byproducts, catalysts, and unreacted reaction substrate and the like, as a reaction substrate in an organic synthesis reaction, and as a catalyst or reaction accelerator in an organic synthesis reaction. Due to its property of reproducibly changing from a soluble state to a solid state according to changes in solution composition, it can be easily separated from the reaction system by solidification after the reaction.

In this way, any compounds added to a reaction involving the lipophilic agent, and byproducts generated in the reaction involving the lipophilic agent, can be easily separated from the reaction system, or a specified reaction substrate or reaction accelerator involving the lipophilic agent can be added to the reaction as a compound which can be easily separated from the reaction system after the completion of the reaction.

Further, in a reaction using the lipophilic agent of the first aspect, the organic synthesis reaction can be carried out at low cost because expensive reagents need not be used excessively as compared with solid phase synthesis, purification becomes straightforward as compared with the effort to be spent on search for a solidification process in a traditional organic synthesis, and large volumes of solvent(s) and labors are saved as otherwise for purification including running silica gel column chromatography. A green era may emerge wherein silica gel chromatography as a basic means for laborious purification for centuries may become obsolete in organic synthesis. This invention may thus lead to a significant revolution in traditional synthetic process development.

Here, the lipophilic agent indicates its use for carrying out organic synthesis reactions, or processes after the reaction, and includes reaction substrates, reaction accelerators, and synthesis building blocks, and the like. The lipophilic agent according to the present invention is not particularly limited in terms of the amount used and can be used in any case such as the case of use in large industrial quantities, or the case of use in small quantities for testing, research or the like.

Further, Lipophilic anchor of the present invention has Lipophilic groups as a portion thereof. In the present invention, Lipophilic group indicates, in the compound shown in Chemical Formula (1), a site having a lipophilic group, and specifically, in the Chemical Formula (1), indicates $R^1$ and $R^2$ attached to triazine core excluding the active site which is X.

The second aspect of the invention provides the lipophilic agent according to the first aspect, characterized in that, in chemical formula (1), X as an active site, is a functional group or functional groups that can be used for the following applications.

"Synthesis building block" indicates a component provided for organic synthesis reaction of the desired compound in the present invention and indicates a general term for a compound which can impart an arbitrary reagent activity to a reaction substrate by introducing a specified functional group via chemical bonding in an arbitrary reaction substrate. Functional groups having the capability to be derivatized or transformed can be used as a synthesis building block. One example containing piperazine (1P) as a secondary amine is shown below.

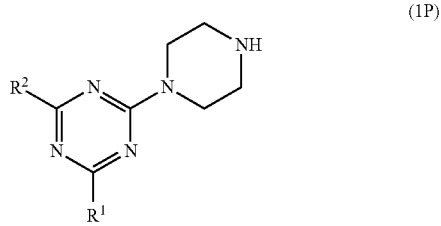

(1P)

"Traceless synthesis" indicates a wide variety of synthetic strategies for preparing target products in a traceless manner where the target products are composed only of the components (atoms, functional groups) inherent to the target core structure. However, almost all the traceless synthesis so far has been carried out on a solid phase support which limits its application for synthesis of a variety of biomolecules on large scale. By attaching a suitable linker to Lipophilic anchor to form a Lipophilic linker, traceless synthesis can be performed in solution. Compounds synthesized on the Lipophilic linker can be released without a trace of the linker that was used to tether the intermediates during the synthesis. This application expands the use of Lipophilic linker from conventional synthesis of biomolecules such as peptides and oligonucleotides to tactical synthesis of a broad range of structural types of organic compounds. Lipophilic agent of this invention may significantly revolutionize synthetic chemistry.

The third aspect of the invention provides the lipophilic agent according to the first or second aspect, wherein $R^1$ and $R^2$ of Chemical Formula (1) are independently selected from the groups comprising alkylamino group or dialkylamino group with a carbon number of 12 to 48 which may have a substituent group and alkoxyl group with a carbon number of 12 to 48 which may have a substituent group shown in the following Chemical Formulas (2, 2' and 2") wherein $R^3$—N—$R^4$ of Chemical Formulas 2, 2' and 2" are 10 of Chemical Formula (1), and $R^5$—N—$R^6$ of Chemical Formula 2, $R^5$—O of Chemical Formula 2', and $R^3$—N—$R^4$ of Chemical Formula 2" is $R^2$ of Chemical Formula (1), respectively.

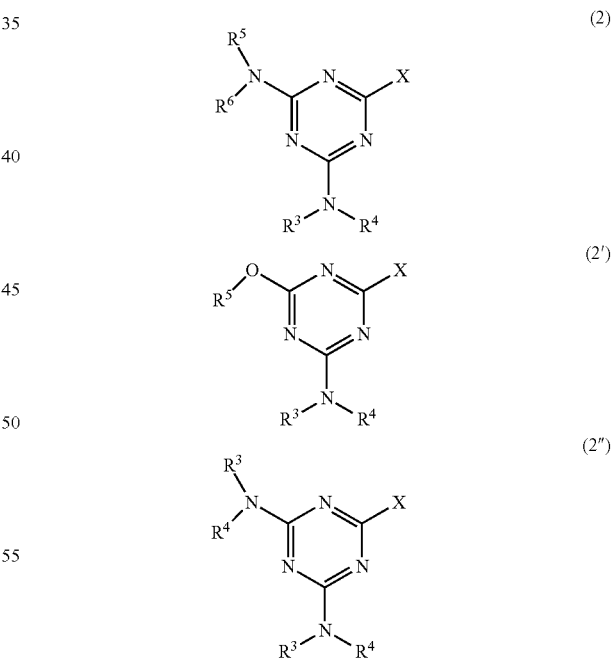

$R^3$, $R^4$ and $R^5$ may be same or different, and are independently selected from the group comprising alkyl group with a carbon number of 12 to 48 which may have a substituent group, and $R^6$ may include a hydrogen atom, or a short alkyl group such as methyl, ethyl, propyl, isopropyl, butyl and the like. Preferably, $R^6$ includes a short alkyl group such as methyl, ethyl, propyl, isopropyl or butyl. Thus, Lipophilic anchor does not have any active proton so as to prevent any possible interference in a multi-step synthesis under a broad range of reaction conditions. Further, in the formula, X represents an active site of the lipophilic agent having one or more atoms selected from the group comprising carbon atom, halogen atom, nitrogen atom, oxygen atom, silicon atom or sulfur atom.

For synthesis of the lipophilic agent shown in Chemical Formula 2 wherein $R^3$, $R^4$, $R^5$ and $R^6$ are different, nucleophilic substitution with one equivalent of a first amine including $R^3$ and $R^4$ proceeds at low temperature between 0° C. and 20° C. to displace the first chloride of cyanuric chloride in presence of a base such as N,N-diisopropylethylamine, followed by nucleophilic substitution with one equivalent of a second amine including $R^5$ and $R^6$ at an elevated temperature between 20° C. to 50° C. to displace the second chloride of cyanuric chloride in presence of a base such as N,N-diisopropylethylamine. Nucleophilic substitution of a third amine such as piperazine as an example to displace the third chloride of cyanuric chloride proceeds at high temperature between 50° C. to 100° C. to give compound 2P. P indicates a secondary amine derived from piperazine. The chemical reaction scheme is shown below:

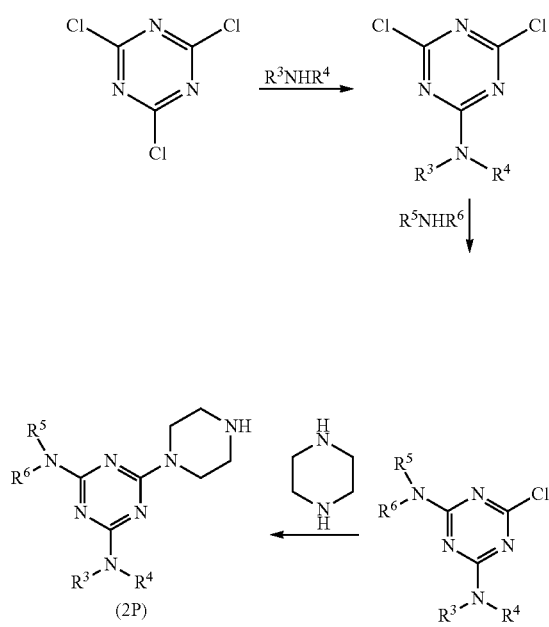

For synthesis of the lipophilic agent shown in Chemical Formula 2' wherein $R^3$, $R^4$ and $R^5$ are same or different, nucleophilic substitution with one equivalent of an alcohol containing $R^5$ proceeds at low temperature between 0° C. and 20° C. to displace the first chloride of cyanuric chloride in presence of a base such as N,N-diisopropylethylamine, followed by nucleophilic substitution with one equivalent of a first amine including $R^3$ and $R^4$ at an elevated temperature between 20° C. to 50° C. to displace the second chloride of cyanuric chloride in presence of a base such as N,N-diisopropylethylamine. Nucleophilic substitution of a second amine such as piperazine as an example to displace the third chloride of cyanuric chloride proceeds at high temperature between 50° C. to 100° C. to give compound 2'P. P indicates a secondary amine derived from piperazine. The chemical reaction scheme is shown below:

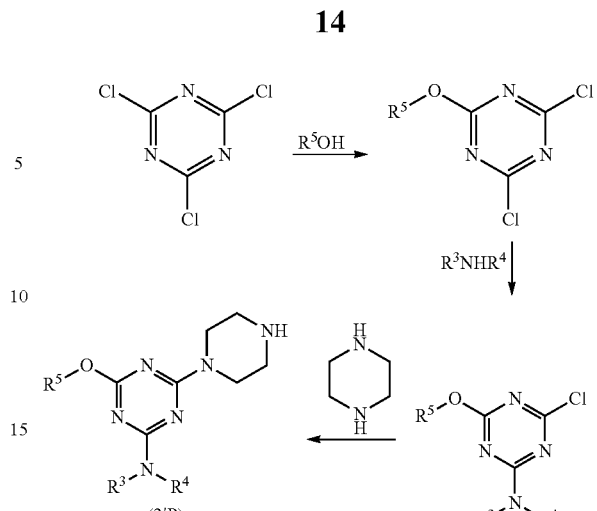

For synthesis of the lipophilic agent shown in Chemical Formula 2" wherein $R^3$, $R^4$ are same or different, use of two equivalents of a first amine including $R^3$ and $R^4$ for nucleophilic substitution displaces two chlorides of cyanuric chloride in presence of a base such as N,N-diisopropylethylamine at an elevated temperature between 20° C. to 50° C. Use of a second amine for nucleophilic substitution displaces a third chloride of cyanuric chloride at high temperature installs an active site X. In the chemical reaction scheme shown below, piperazine as a second amine as an example displaces a third chloride of cyanuric chloride at high temperature between 50° C. to 100° C. to give compound 2"P which installs piperazine as an active site. P indicates a secondary amine derived from piperazine.

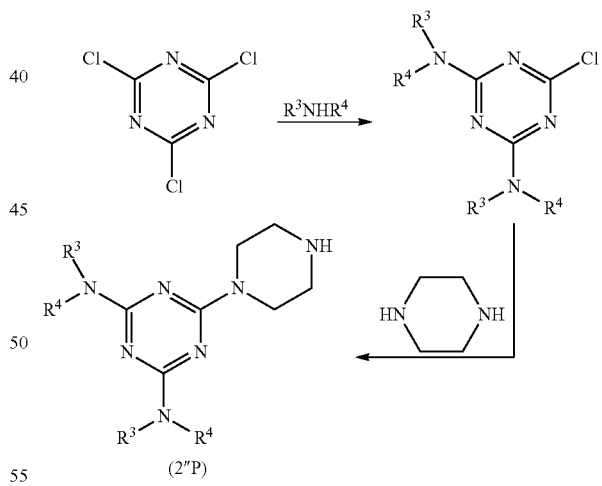

The fourth aspect of the invention provides the lipophilic agent according to the third aspect, wherein in the Chemical Formulas (2, 2' and 2"), $R^3$, $R^4$ and $R^5$ are n-octadecyl group and $R^6$ is a methyl group shown by the following Chemical Formulas (3M, 3G and 3Q) (M indicates melamine core, its basic structure being 2,4,6-triamino-1,3,5-triazine. G indicates guanamine core, a structure closely related to melamine except with one substituent other than amino group. Q indicates a melamine core containing quadruple n-octadecyl groups):

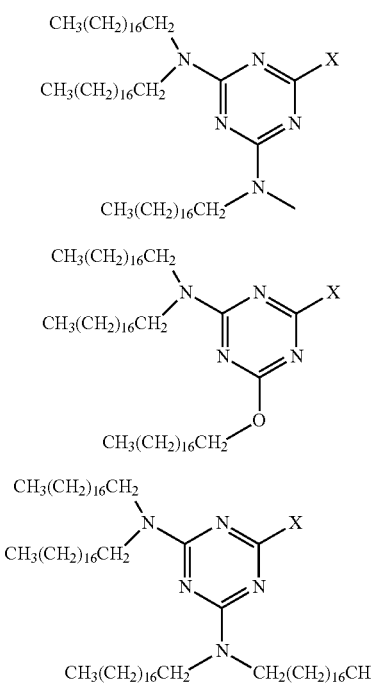

(3M)

(3G)

(3Q)

and X represents an active site of the lipophilic agent having one or more atoms selected from the group comprising carbon atom, halogen atom, nitrogen atom, oxygen atom, silicon atom or sulfur atom. The lipophilic agents (3M) and (3G) according to the fourth aspect have three n-octadecyl groups and the lipophilic agent (3Q) has four n-octadecyl groups. They each can be dissolved uniformly at high concentration in many organic solvents and can react with a high degree of reactivity with other compounds in many organic solvents.

Lipophilic agents as shown by Chemical Formula (3M, 3G and 3Q) can connect, for example, with a diamine such as piperazine to provide an active site containing a secondary amine. The corresponding structures (3MP, 3GP, 3QP) are shown below. P indicates a secondary amine derived from piperazine.

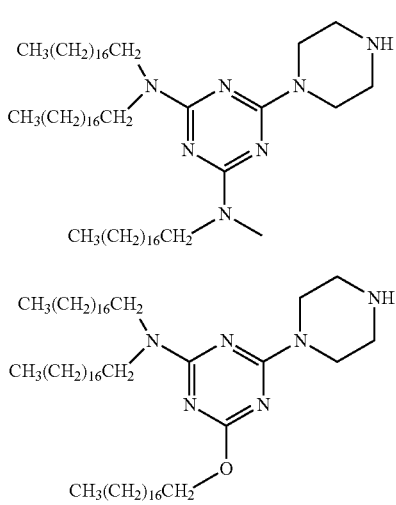

(3MP)

(3GP)

-continued

(3QP)

Thus, for synthesis of the lipophilic agent 3QP as an example, use of two equivalents of di(n-octadecyl)amine for nucleophilic substitution at temperature between 20° C. to 50° C. displaces two chlorides of cyanuric chloride in presence of a base such as N,N-diisopropylethylamine. Use of piperazine for nucleophilic substitution displaces a third chloride of cyanuric chloride at high temperature between 50° C. to 100° C. to give compound 3QP which installs piperazine as an active site.

The lipophilic agent as shown by Chemical Formula (3M, 3G and 3Q) can connect with an amino acid such as isonipecotic acid to provide an active site containing a carboxylic acid. Its structure (3C derivatized from 3Q as an example) is shown below:

(3C)

The lipophilic agent as shown by Chemical Formula (3M, 3G and 3Q) can connect with an amino alcohol such as 4-piperidinemethanol to provide an active site containing an alcohol. Its structure (3H derivatized from 3Q as an example) is shown below:

(3H)

The lipophilic agent 3H containing a hydroxyl group, as an example, can function as a linker to generally form an ester bond with a carboxyl group of a target compound. After a mission for a multi-step synthesis of a target molecule is accomplished, the linkage can be cleaved to give the target molecule with carboxylate by sodium hydroxide, hydrazide by hydrazine, amide by ammonia, alcohol by lithium borohydride, while the linker can be easily recovered as its original form, and therefore can be re-used for a subsequent mission to synthesize the same target molecule or a different target molecule. Thus, the linker can be technically used over and over again for virtually unlimited rounds of mission, providing the green benefit (saving the resources and protecting the environment) for a multi-step synthesis within a mission and for further missions.

Further, the lipophilic agent (3MP, 3GP, 3QP) according to the fourth aspect is useful for a multi-step synthesis of a biomolecule such as a peptide after the lipophilic agent is derivatized to form corresponding amide bond with suitable reagent to install functional linkers. The nature of the linker determines the chemistry to be used for the synthesis, and especially the conditions under which the biomolecule can be cleaved from the Lipophilic linker.

General procedure in an organic reaction using the lipophilic linker for synthesis of a biomolecule comprises the following steps for each cycle:

(a) dissolving the lipophilic linker in a reaction solvent system.

(b) reacting the lipophilic linker with a target compound.

(c) precipitating a derivative of the lipophilic linker and the target compound from the reaction solvent system by reproducibly changing the derivative from a soluble state to a solid state according to changes in solution composition. The change in solution composition comprises adding a poor solvent with respect to the lipophilic derivative to the reaction system.

(d) using a suction filter to carry out the solid liquid separation to obtain the derivative.

Common linkers include, but are not limited to, the following.

Lipophilic-Carboxylic acid linker (3A derivatized from 3QP as an example): The linker can be formed with succinic anhydride and used for synthesis of a biomolecule commonly containing a hydroxyl group. The ester linkage thus formed can be ultimately cleaved to give the biomolecule product with hydroxyl group by using sodium hydroxide, hydrazine, or ammonia.

Lipophilic-HMBA linker (3B derivatized from 3QP as an example): The linker can be formed as hydroxymethylbenzamide (HMBA) and used for synthesis of a target molecule such as a peptide. The hydroxyl can form an ester bond with an amino acid of a peptide with defined sequence and can be ultimately cleaved to give peptide product at the C-terminal with carboxylate by sodium hydroxide, hydrazide by hydrazine, amide by ammonia, alcohol by lithium borohydride.

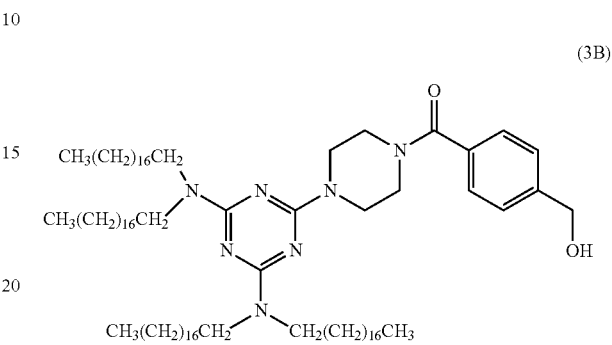

(3B)

Lipophilic-p-Oxybenzyl Alcohol linker (3W derivatized from 3QP as an example): The linker contains the functional group of p-oxybenzyl alcohol and can be used for synthesis of a target biomolecule such as a peptide. When the Lipophilic linker (3W) is used for a peptide synthesis reaction, the hydroxyl can form an ester bond with an amino acid as a first target compound to give a lipophilic derivative containing the first amino acid. Further amino acids are sequentially extended by reacting with the amino acid of the corresponding lipophilic derivative, namely, an amino acid extension reaction step proceeds in which another amino acid is reacted with the amino acid of the lipophilic derivative. After completion of the amino acid extension reaction step with a defined sequence, a step of separating the synthesized peptide from the lipophilic linker is carried out by adding an acid such as 90-95% trifluoroacetic acid (TFA) to give peptide product at the C-terminal with carboxylic acid.

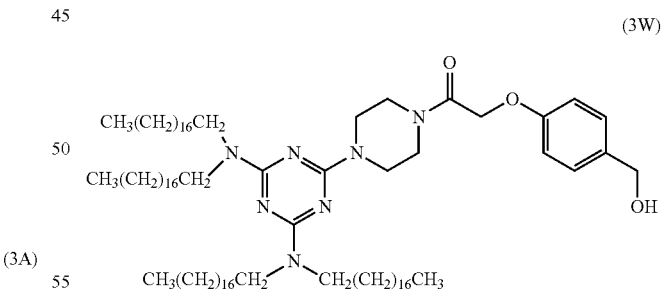

(3W)

Lipophilic-Trityl-OH linker (3T derivatized from 3QP as an example): The linker contains the functional group of trityl alcohol. The hydroxyl group of the trityl alcohol is a stable form for storage, and it has to be chlorinated to form the trityl chloride compound before use. The linker can be used for synthesis of biomolecules such as peptide. The linkage formed from an ester bond with an amino acid of a peptide with defined sequence can be ultimately cleaved to give peptide product at the C-terminal with carboxylic acid in 1-5% TFA in dichloromethane.

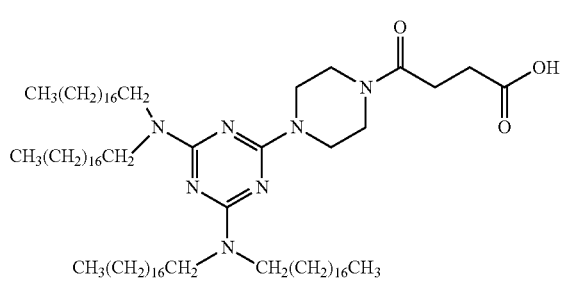

(3A)

(3T)

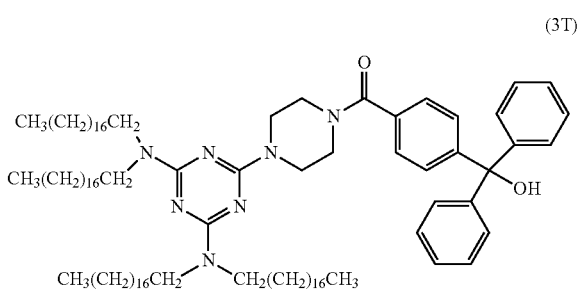

Lipophilic-Rink Amide linker (3R derivatized from 3QP as an example): The Lipophilic reagent (3QP) can be functionalized with an amino group and used for synthesis of biomolecules such as peptide. The linkage formed from an amide bond with an amino acid of a peptide with defined sequence can be ultimately cleaved to give peptide product at the C-terminal with amide by 50% TFA in dichloromethane in 1 hour.

(3R)

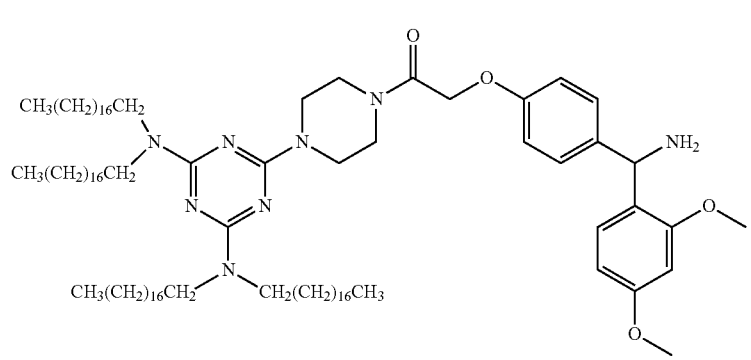

Furthermore, Lipophilic agent of the present embodiment may be a compound shown by the following Chemical Formula (3QP).

(3QP)

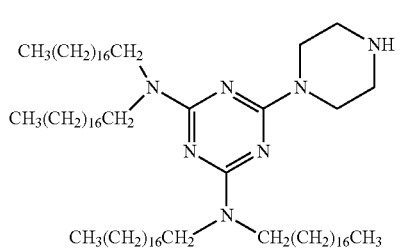

Namely, the compound shown by the Chemical Formula (3QP) is a Lipophilic agent shown by the Chemical Formula (1), wherein in the Chemical Formula (1), X is a piperazine group, $R^1$ and $R^2$ are both N,N-di(n-octadecyl)amino group. Or, the compound shown by the Chemical Formula (3QP) is a Lipophilic agent shown by the Chemical Formula (2"), wherein in the Chemical Formula (2"), X is a piperazine group, $R^3$ and $R^4$ are both n-octadecyl group. Lipophilic agent 3QP is, thus preferably, the structure of Chemical Formula (1) including a triazine core having Lipophilic groups $R^1$ and $R^2$ where $R^1$ and $R^2$ are both N,N-di(n-octadecyl)amino group. The amino functional group in piperazine is reactive to form a variety of derivatives that are useful for further organic synthesis of biomolecules.

Manufacturing Method of Lipophilic Agent

The manufacturing method of the lipophilic agent indicated in the above formula is not particularly limited, but it can generally be synthesized by using cyanuric chloride as the starting material, taking advantage of its easy manipulation of three independent, readily tunable ring positions, which facilitates the sequential nucleophilic substitution reactions with a variety of nucleophiles containing sulfur, oxygen and nitrogen. The triazine core is thus used as a privileged structure for assembly of lipophilic agent of this invention.

Cyanuric chloride having three chloride atoms can react sequentially with nucleophiles containing oxygen of an alcohol, sulfur of a thiol, or nitrogen of an amine. The first nucleophilic substitution can proceed at low temperature between 0° C. and 20° C. with a nucleophile containing oxygen of an alcohol, sulfur of a thiol, and nitrogen of an amine. The second nucleophilic substitution can proceed at an elevated temperature between 20° C. to 50° C. with a nucleophile containing nitrogen of an amine. The third nucleophilic substitution can proceed at higher temperature between 50° C. to 100° C. with a nucleophile containing nitrogen of an amine. Lipophilic agent is thus prepared with a triazine core having specified Lipophilic groups from nucleophilic substitution of nucleophiles containing oxygen of an alcohol, sulfur of a thiol, and nitrogen of an amine with lipophilic groups with a carbon number of 12 to 48 which may have a substituent group.

Method of Organic Synthesis Reaction

The lipophilic agent of the present embodiment can be used by the same method of common use as the reagent used in the solution phase organic synthesis reactions which do not have lipophilic groups. Namely, in a state wherein the reaction substrate to be reacted is dissolved or dispersed in a solvent, the lipophilic agent having reactive site(s) or functional group(s) is added, and a reaction is carried out. Here, as the solvent used in the reaction system, it is possible to use a general organic solvent in the reaction, but because the reactivity is increased as the solubility of the lipophilic agent in the solvent increases, it is preferable to select a solvent for which the solubility of the lipophilic agent is high. Specifically, toluene, xylenes (including o-xylene, m-xylene, p-xylene, or a mixture of them), benzotrifluoride, tetrahydrofuran (THF), t-butyl methyl ether, hexane, heptane, cyclohexane and the like are preferable, but it is not particularly limited to those. Dichloromethane, 1,2-dichloroethane and chloroform are useful, but not desirable due to their environmental hazards and toxic health consequences. To confirm the progress of the reaction, same methods used for general solution phase organic synthesis reactions can be applied. Namely, thin layer silica gel chromatography, high speed liquid chromatography and the like can be used to track the reaction.

Reaction Applications

In a reaction step, by reacting a specified reaction substrate and the lipophilic agent of the present embodiment having reactive site(s) or functional group(s), it is possible to obtain a desired Lipophilic derivative. Further, it is possible to carry out an arbitrary chemical reaction for obtaining a desired compound and reacting residual reaction substrate added in excess to the reaction system, and byproducts, with the lipophilic agent having reactive site(s) or functional group(s) to remove the residual reaction substrate added in excess to the reaction system, and byproducts formed in the reaction system. Applications of the lipophilic agent of the present embodiment are, but not limited to, the use as a nucleophilic scavenger and an electrophilic scavenger, as a synthesis building block. More importantly, the lipophilic agent of the present embodiment can be used for synthesis of biomolecules, especially macromolecules such as oligonucleotides and peptides.

Use of the Lipophilic Agent as a Synthesis Building Block

In the case of using the lipophilic agent of the present embodiment as a synthesis building block, for example, consideration can be given to using the lipophilic agent as a reaction substrate in a nucleophilic addition reaction, nucleophilic substitution reaction, dehydration condensation reaction, and the like. As a reagent for organic synthesis reaction which can be used in such a reaction, there is no particular limitation, and for example, in the lipophilic agent shown in Chemical Formula (1), the lipophilic agent where X is an active site shown by (1P), (1C), and (1H) can be mentioned. As the solvent used for the reaction, any solvent which can be ordinarily used for these reactions can be used, and in the present embodiment, from the point of solubility of the lipophilic agent having lipophilic groups, it is possible to use toluene, xylenes (including o-xylene, m-xylene, p-xylene, or a mixture of them), benzotrifluoride, tetrahydrofuran (THF), t-butyl methyl ether, hexane, heptane, cyclohexane and the like.

Use e of the Lipophilic Agent for Peptide Synthesis

Among the lipophilic agent of the present embodiment, the structure shown by Chemical Formula (1) where X contains a p-oxybenzyl alcohol moiety as a functional linker indicated by (1W), is especially useful for peptide synthesis. After condensation of carboxyl group of an amino acid with the alcohol group of the Lipophilic linker (1W) to form an ester bond, the amino acid forms a Lipophilic derivative as a C-terminal carboxy-protecting group which functions as an anchor group for continuous peptide elongation. Thus, the peptide synthesis reaction can be carried out by sequentially forming bonds to an activated amino acid in the state wherein the carboxyl group is bonded to Lipophilic linker. After each step of peptide synthesis, the peptide on Lipophilic linker can be collected as a sold by changes in the solution composition, whereas excess residual reaction substrates are still in the reaction solution system and can be removed by filtration. At the completion of the peptide synthesis reaction, by adding acidic reagent such as trifluoroacetic acid (TFA) to Lipophilic linker-containing peptide, the peptide can be obtained by detaching from the Lipophilic linker. Thus, by tethering with Lipophilic linker, the synthesis method provides an easy purification process for each step of peptide elongation and removes the limitation for large scale synthesis.

Applications of Lipophilic linker tethering a reactive site of p-oxybenzyl alcohol (1W) as a functional linker are representative for peptide synthesis. Further, Lipophilic linker tethering a hydroxyl functional group derivatized from 4-hydroxymethylbenzoic acid linker (1B), Lipophilic linker tethering a trityl chloride converted from trityl alcohol linker (1T), Lipophilic linker tethering a Rink Amide linker (1R) are commonly used for peptide synthesis. The nature of the linker determines the chemistry to be used, and especially the conditions under which the products can be cleaved from Lipophilic linker. For example, the Lipophilic linker (1B) can be cleaved to give peptide product at the C-terminal with carboxylate by sodium hydroxide, hydrazide by hydrazine, amide by ammonia, alcohol by lithium borohydride; the Lipophilic linker (1T) can be cleaved to give peptide product at the C-terminal with carboxylic acid in 1-5% TFA in dichloromethane in 1 minute; the Lipophilic linker (1R) can be cleaved to give peptide product at the C-terminal with amide by 50% TFA in dichloromethane in 1 hour.

Separation by Changing the Solution Composition

The lipophilic agent of the present embodiment responds sharply to changes in the solution composition and crystallize. Because of this, it is possible to solidify (or crystallize) the lipophilic agent and the resultant Lipophilic derivative using the means of changing the composition of the solution.

As a preferred means for changing the solution composition, for example, the means of adding a poor solvent for the lipophilic agent and the resultant Lipophilic derivative to the reaction solution can be mentioned. A poor solvent is a solvent miscible with the reaction solvent, but results in precipitation or solidification of the lipophilic agent and/or the resultant Lipophilic derivative. Here, by adding a poor solvent which is highly miscible with the reaction solvent, there is no phase separation of the solution phase, and thus it is possible to easily change the solution composition. As the poor solvent, it is possible to use the same solvent used as the reaction solvent, or a solvent which differs from the reaction solvent. For example, in the case of using toluene, xylenes (including o-xylene, m-xylene, p-xylene, or a mixture of them), benzotrifluoride, tetrahydrofuran (THF), t-butyl methyl ether, hexane, heptane, cyclohexane and the like as the reaction solvent, it is possible to use methanol, ethanol, isopropanol, 2,2,2-trifluoroethanol, acetonitrile, acetone, methyl ethyl ketone, ethyl acetate, acetic acid, N,N-dimethylformamide (DMF), dimethyl sulphoxide (DMSO) and the like as the poor solvent. In the case of using mixed solvents such as THF and DMF as an example, it is possible to use methanol, ethanol, isopropanol, 2,2,2-trifluoroethanol, acetonitrile, acetone, methyl ethyl ketone, ethyl acetate, acetic acid, dimethyl sulphoxide (DMSO) and the like as the poor solvent, and it is also possible to use DMF as the poor solvent. By adding the poor solvent to the reaction solution, the polarity of the solution increases, and the lipophilic agent or the resultant Lipophilic derivative can crystallize and solid liquid separation becomes possible. A suction filter can be used to carry out the solid liquid separation.

V. EFFECTS OF THE INVENTION

According to the present invention, the lipophilic agent can be uniformly dissolved in many organic solvents, and thus can be reacted with a high degree of reactivity with other compounds to form Lipophilic derivative. Further, after the reaction, it is possible to choose from many separation methods such as a solid liquid separation method by crystallizing the Lipophilic derivative, or a liquid-liquid extraction method by adding a separation solvent which is immiscible with the reaction solvent and partitioning the Lipophilic derivative into the separation solvent. Because the separation conditions of these separation methods can be uniformly determined based on the property of the Lipophilic anchor as a key component of Lipophilic derivative, it is not necessary to consider the separation conditions based on the characteristic properties or the like of each organic synthesis reaction. This not only simplifies process development, but also, for example, makes it possible to accelerate the research and development of pharmaceuticals and the like by compound library synthesis and the like, and this can in turn contribute to technical innovations in the chemical industry.

Further, the lipophilic agent, after a mission for a multi-step synthesis of a target molecule is accomplished, and proper recovery is achieved to regenerate its original form, can be re-used for a new mission to synthesize the same target molecule or a different target molecule. Thus, the lipophilic agent can be recycled and reused over and over again. Synthesis of the lipophilic agent of the present invention does not use especially expensive compounds, synthesis using the lipophilic agent does not need large excess reactants, pure solid Lipophilic derivatives can be obtained by simply precipitating with change of solution composition followed by filtering to obtain the desired material with minimal solvent consumption and labor involvement, the lipophilic agent can be regenerated after completion of a multi-step synthesis, altogether implicating the significance of the organic synthesis using the lipophilic agent that can be carried out economically and representing a tremendous step forward for greening chemical processes to boost productivity, save resources and protect the environment.

VI. INDUSTRIAL APPLICABILITY

According to the production method using the lipophilic agent for organic synthesis, reactants are soluble in one system of solvent(s). Suitable compound tethered with the lipophilic agent can proceed reaction in a homogeneous solution and is insoluble in other system of solvent(s) so that the desired compounds can be isolated as a purified solid. The method facilitates the isolation of purified product from a reaction mixture and obviate the needs of traditional column chromatography which is time-consuming and solvent-wasting. More importantly, for synthesis of biomolecules such as peptides and oligonucleotides, by performing precipitation and solid-liquid separation by addition of a poor solvent or poor solvents to change the solvent composition after peptide elongation or oligonucleotide elongation, the method facilitates the isolation of purified intermediates and final product from a reaction mixture and obviate the needs of conventional solid support which limits the scale of production. Therefore, a convenient and efficient production method of pharmaceuticals such as peptides or oligonucleotides, which enables scaling up and is suitable for industrial production can be provided.

EXAMPLES

The present invention is explained below with reference to the following examples, but the present invention is not in any way limited by these examples. The practice of the present invention will employ, unless otherwise indicated, techniques of synthetic organic chemistry, biochemistry and the like, which are within the skill of the art. Such techniques are explained fully in the literature. See, for example, Kirk-Othmer's Encyclopedia of Chemical Technology; and House's Modern Synthetic Reactions.

The following examples are put forth so as to provide those of ordinary skill in the art with a complete disclosure and description of how to make and use the compositions/compound/methods of the invention. Efforts have been made to ensure accuracy with respect to numbers (e.g., amounts, temperature, etc.) but some experimental error and deviations should, of course, be allowed. All components were obtained commercially unless otherwise indicated.

Example 1

Synthesis of 2-(4'-piperazino)-4-(N-methyl-N-n-octadecyl)amino-6-[N,N-di(n-octadecyl)amino]-1,3,5-triazine (3MP)

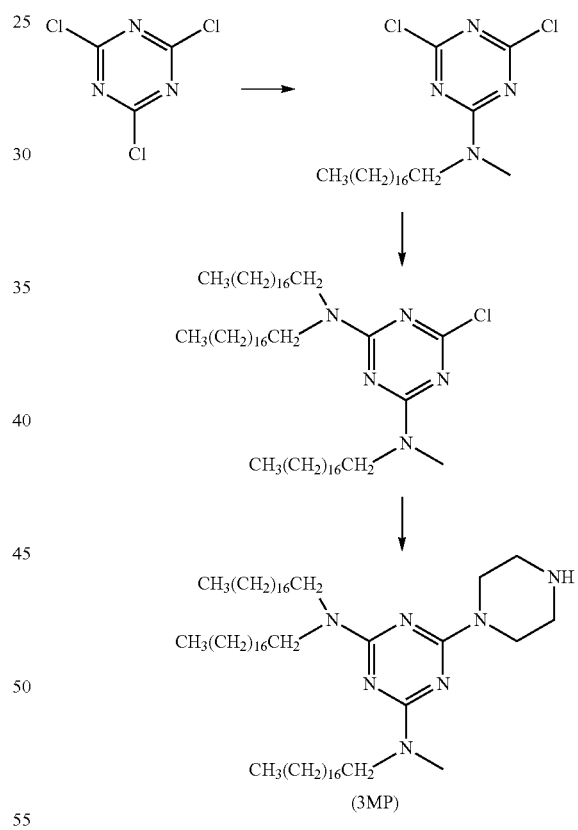

Cyanuric chloride (5 g, 27.1 mmol) was dissolved in toluene (200 mL), and mixed with N,N-diisopropylethylamine (DIPEA) (18.5 ml, 108.8 mmol). N-Methyl-N-n-octadecylamine (7.68 g, 27.1 mmol) was added to the mixture cooled in an ice bath. This was stirred for 4 hours, and then the mixture was allowed to warm to room temperature. Di(n-octadecyl)amine (14.15 g, 27.1 mmol) was added to the mixture. This was stirred for 16 hours at room temperature. After the completion of the reaction, ethanol (400 mL) was added, and after the precipitation, suction filtration was carried out and solid product, 2-chloro-4-(N-methyl-N-n- octadecyl)amino-6-[N,N-di(n-octadecyl)amino]-1,3,5-triazine (23.6 g, 95%), was obtained.

2-Chloro-4-(N-methyl-N-n-octadecyl)amino-6-[N,N-di(n-octadecyl)amino]-1,3,5-triazine (20 g, 21.8 mmol) was dissolved in toluene (300 mL). Piperazine (10 g, 116 mmol) dissolved in isopropanol (100 mL) was added to the mixture. This was stirred for 16 hours at 80° C. After completion of the reaction, most solvents were removed by evaporation. Ethanol was added to the residue and after the precipitation, suction filtration was carried out and solid product, 2-(4'-piperazino)-4-(N-methyl-N-n-octadecyl)amino-6-[N,N-di(n-octadecyl)amino]-1,3,5-triazine (20.4 g, 97%), was obtained.

Example 2

Synthesis of 2-(4'-piperazino)-4-n-octadecyloxy-6-[N,N-di(n-octadecyl)amino]-1,3,5-triazine (3GP)

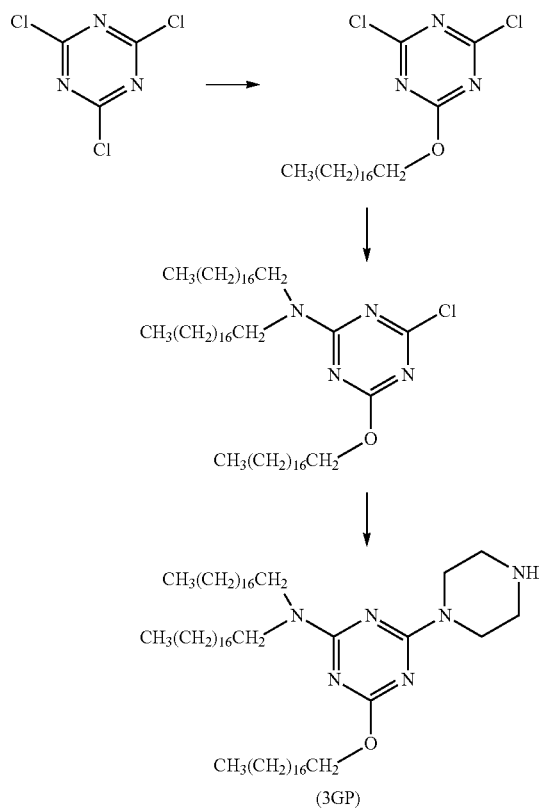

Cyanuric chloride (25 g, 135.6 mmol) was dissolved in toluene (1 L), and mixed with DIPEA (92.23 ml, 542.32 mmol). n-Octadecyl alcohol (37.4 g, 138.26 mmol) was added to the mixture cooled in an ice bath. This was stirred for 4 hours, and then the mixture was allowed to warm to room temperature and continued stirred for 12 hours. Di(n-octadecyl)amine (78.63 g, 150.64 mmol) was added to the mixture. This was stirred for 16 hours at room temperature. After the completion of the reaction, ethanol (1 L) was added, and after the precipitation, suction filtration was carried out and solid product, 2-chloro-4-n-octadecyloxy-6-[N,N-di(n-octadecyl)amino]-1,3,5-triazine (121.6 g, 99%), was obtained.

2-Chloro-4-n-octadecyloxy-6-[N,N-di(n-octadecyl)amino]-1,3,5-triazine (40 g, 44 mmol) was dissolved in toluene (500 ml). Piperazine (20 g, 232 mmol) dissolved in isopropanol (200 mL) was added to the mixture. This was stirred for 16 hours at 50° C. After completion of the reaction, most solvents were removed by evaporation. Ethanol was added to the residue and after the precipitation, suction filtration was carried out and solid product, 2-(4'-piperazino)-4-n-octadecyloxy-6-[N,N-di(n-octadecyl)amino]-1,3,5-triazine (29.6 g, 71%), was obtained.

Example 3

Synthesis of 2-(4'-piperazino)-4,6-di[N,N-di(n-octadecyl)amino]-1,3,5-triazine (3QP)

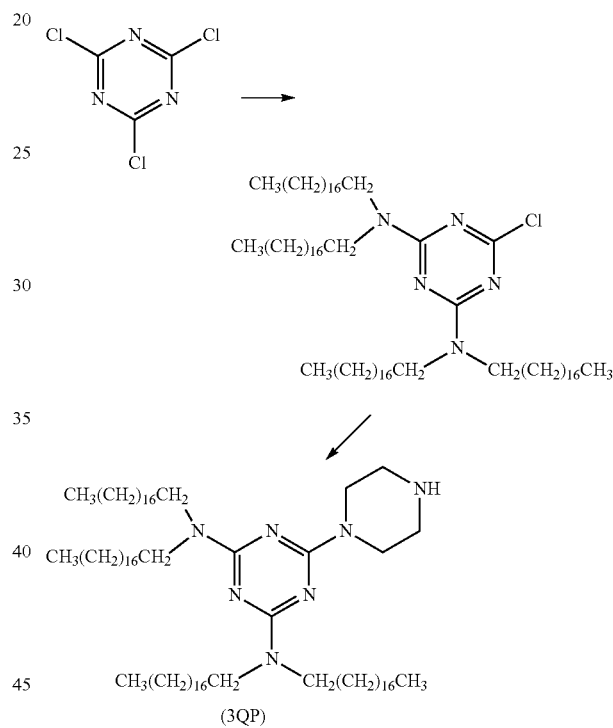

Cyanuric chloride (10 g, 54.2 mmol) was dissolved in toluene (400 mL), and mixed with DIPEA (37 ml, 217.6 mmol). Di(n-octadecyl)amine (56.6 g, 108.4 mmol) was added to the mixture cooled in an ice bath. After addition, the ice bath was removed. This was stirred for 16 hours at room temperature. After the completion of the reaction, ethanol (800 mL) was added, and after the precipitation, suction filtration was carried out and solid product, 2-chloro-4,6-di[N,N-di(n-octadecyl)amino]-1,3,5-triazine (55.7 g, 89%), was obtained.

2-Chloro-4,6-di[N,N-di(n-octadecyl)amino]-1,3,5-triazine (25 g, 21.6 mmol) was dissolved in toluene (375 mL). Piperazine (10 g, 116 mmol) dissolved in isopropanol (100 mL) was added to the mixture. This was stirred for 16 hours at 80° C. After completion of the reaction, ethanol was added and after the precipitation, suction filtration was carried out and solid product, 2-(4'-piperazino)-4,6-di[N,N-di(n-octadecyl)amino]-1,3,5-triazine (25.1 g, 96%), was obtained.

Example 4

Synthesis of Lipophilic Linker Containing p-oxybenzyl Alcohol (3W)

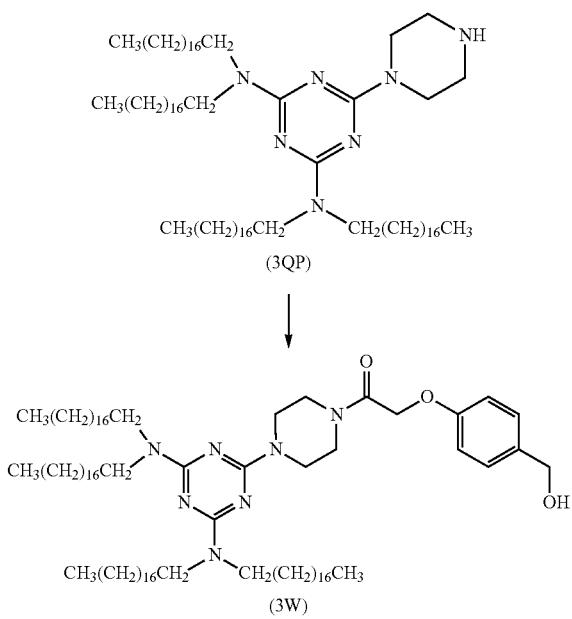

2-(4'-piperazino)-4,6-di[N,N-di(n-octadecyl)amino]-1,3,5-triazine (3QP) (2.41 g, 2.00 mmol) was dissolved in toluene (20 ml). 4-(Hydroxymethyl)phenoxyacetic acid (373 mg, 2.05 mmol), and N,N'-diisopropylcarbodiimide (DIC) (265 mg, 2.10 mmol) were then added to the solution for the condensation reaction. The reaction mixture was stirred at room temperature until the reaction was completed (30 min). After completion, acetonitrile was added to the reaction mixture to give the solid product, the Lipophilic linker (3W) (2.73 g) quantitatively as a precipitate. The precipitate was filtered and washed with acetonitrile.

Example 5

Synthesis of Peptide Using Lipophilic Linker-3W

Acetyl tetrapeptide-2 was synthesized using Lipophilic linker-3W. This four amino acid peptide could mimic the youth hormone called thymopoietin. By compensating the loss of thymic factors that come with age, the peptide can stimulate the skin immune defenses and help the skin to regenerate. The peptide has the following structure: N2-acetyl-L-lysyl-L-alpha-aspartyl-L-valyl-L-tyrosine. The synthesis was carried out by the following general procedures using Fmoc-O-tert-butyl-L-tyrosine, Fmoc-L-valine, Fmoc-L-aspartic acid 4-tert-butyl ester, Na-Fmoc-Ne-Boc-L-lysine and acetic acid sequentially.

General Procedure for Adding the First Fmoc-Amino Acid

Lipophilic linker-3W was dissolved in toluene (1 mmole/10 ml). Fmoc-amino acid (1.5 equivalents), N,N'-diisopropylcarbodiimide (DIC) (1.5 equivalents), and 4-(N,N-dimethylamino)pyridine (DMAP) (0.2 equivalents) were then added to the solution. The reaction mixture was stirred at room temperature until the reaction was completed (30 min). After completion, acetonitrile was added to the reaction mixture to give the product quantitatively as a precipitate. The precipitate was filtered and washed with acetonitrile.

General Procedure for Coupling of Fmoc-Amino Acid

To a solution of Lipophilic linker-3W tagged peptide in THF (0.10 M), respective Fmoc-amino acid (1.2 mol equiv.), O-(1H-benzotriaol-1-yl)-N,N,N',N'-tetramethyluronium hexafluorophosphate (HBTU) (1.2 mol equiv.), 1-Hydroxybenzotriazole (HOBt) (1.2 mol equiv.), and DIPEA (2.4 mol equiv.) were added. The resulting reaction mixture was stirred at room temperature until completion of the reaction (determined by TLC), followed by dilution with acetonitrile to give a product as a precipitate.

General Procedure for Basic Deprotection of Lipophilic Linker-3W Tagged Peptide Lipophilic linker-3W tagged peptide was dissolved in 1% piperidine and 1% 1,8-diazabicyclo[5.4.0]undec-7-ene (DBU) in THF (0.10 M). The resulting reaction mixture was stirred at room temperature until completion of the reaction (determined by TLC), followed by adding acetonitrile to give a product as a precipitate.

General Procedure for Final Cleavage of Peptide from Lipophilic Linker-3W

Lipophilic linker-3W tagged peptide was dissolved in 2.5% triisopropylsilane (TIS) and 2.5% water in trifluoroacetic acid (TFA). The reaction mixture was stirred at room temperature until the reaction was completed. After completion, the solution was diluted with ethanol and the precipitate was removed by filtration, and t-butyl methyl ether was added to the filtrate to give the peptide quantitatively as a precipitate.

What is claimed is:

1. A compound having, a chemical formula selected from the group consisting of 3QP, 3C, 3H, 3A, 3B, 3W, 3T and 3R, wherein 3QP, 3C, 3H, 3A, 3B, 3W, 3T and 3R have the respective structures:

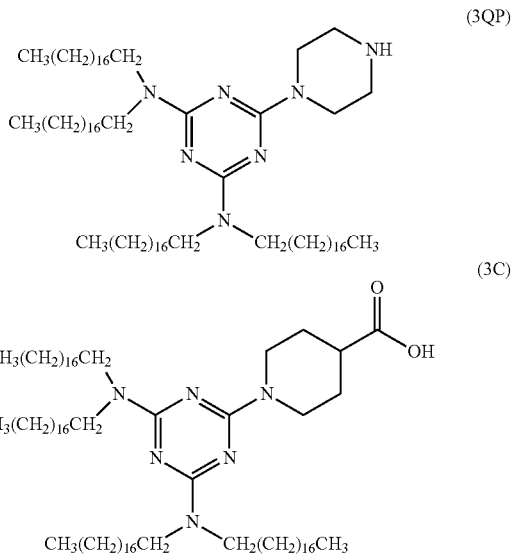

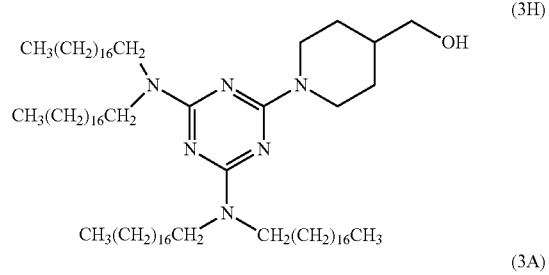
(3H)
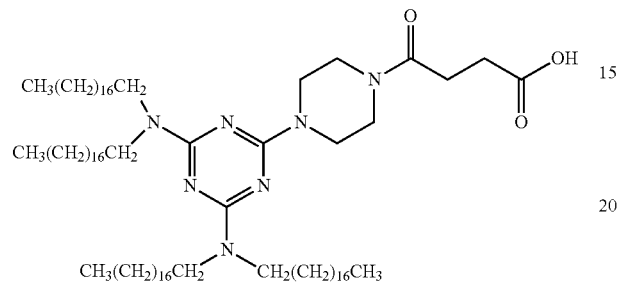
(3A)
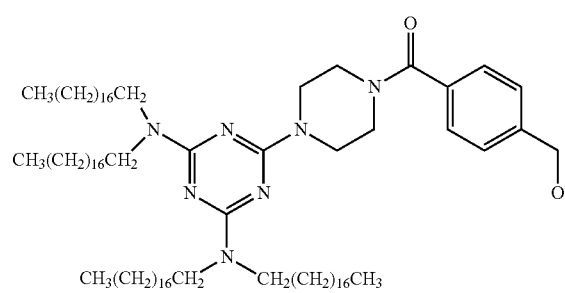
(3B)
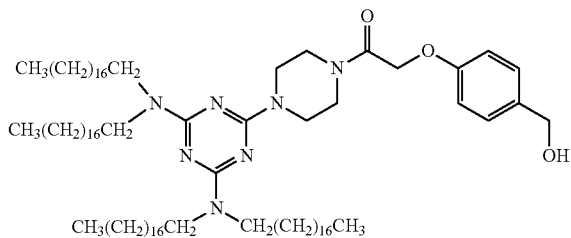
(3W)
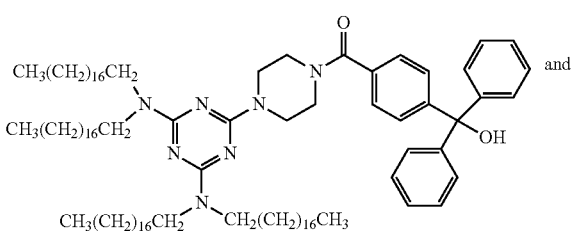
(3T)
and
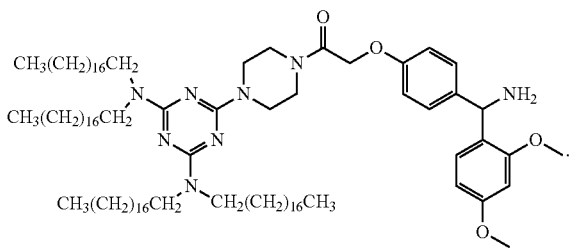
(3R)
2. The compound of claim 1, wherein the compound is effective to form a solid product from a chemical reaction after adding a poor solvent.
3. The compound of claim 2, wherein the poor solvent is methanol or acetonitrile.
* * * * *

UNITED STATES PATENT AND TRADEMARK OFFICE
CERTIFICATE OF CORRECTION

| | | |
|---|---|---|
| PATENT NO. | : 12,428,385 B2 | Page 1 of 1 |
| APPLICATION NO. | : 17/748292 | |
| DATED | : September 30, 2025 | |
| INVENTOR(S) | : Li | |

It is certified that error appears in the above-identified patent and that said Letters Patent is hereby corrected as shown below:

On the Title Page

Item (73) Please change "ASSIGNEE" "Brotide Core, LLC" to --Biotide Core, LLC--.

Signed and Sealed this
Twenty-fifth Day of November, 2025

John A. Squires
*Director of the United States Patent and Trademark Office*